United States Patent [19]

Perlin

[11] Patent Number: 4,777,949
[45] Date of Patent: Oct. 18, 1988

[54] SURGICAL CLIP FOR CLAMPING SMALL BLOOD VESSELS IN BRAIN SURGERY AND THE LIKE

[75] Inventor: Alfred R. Perlin, Highland Park, Ill.
[73] Assignee: Metatech Corporation, Wheeling, Ill.
[21] Appl. No.: 48,002
[22] Filed: May 8, 1987
[51] Int. Cl.$^4$ ............................................. A61B 17/12
[52] U.S. Cl. ................................... 128/325; 128/346; 24/546
[58] Field of Search ...................... 128/346, 325, 326; 24/67.9, 67 R, 546

[56] References Cited

U.S. PATENT DOCUMENTS

| | | | |
|---|---|---|---|
| 4,024,868 | 5/1977 | Williams | 128/346 |
| 4,444,187 | 4/1984 | Perlin | 128/346 |
| 4,660,558 | 4/1987 | Kees | 128/346 X |

Primary Examiner—Michael H. Thaler

[57] ABSTRACT

A miniature surgical clip made of a single continuous length of spring material comprising, in combination, first and second operating members arranged at an acute angle with respect to one another connected together at a common apex, the first operating member having an inwardly bent base leg which defines a guide element and a first jaw member which extends from the base leg in a direction away from the common apex. The second operating member includes a portion defining a second jaw member which extends adjacent to and beyond the guide element in a direction away from the common apex and substantially parallel to the first jaw member to form cooperating jaws which are straight and parallel. The second jaw member includes an additional portion which is sharply bent back along the second jaw member and slidingly grasps the guide element between the second jaw member and the additional portion, whereby the operating members are outwardly sprung with respect to one another for biasing the first and second jaw members resiliently into clamping engagement such that when a mutually inward force is applied to the operating members, the first and second jaw members are spread apart for engagement of a blood vessel between them, and such that, when the mutually inward force is released, the second jaw member is guided by the guide element towards the first jaw member and into directly opposed clamping engagement with the blood vessel.

5 Claims, 3 Drawing Sheets

SURGICAL CLIP FOR CLAMPING SMALL BLOOD VESSELS IN BRAIN SURGERY AND THE LIKE

In brain surgery it is frequently necessary to clamp the numerous small blood vessels which tend to bleed profusely, not only to prevent excessive loss of blood by the patient but in order to keep a reasonably clear operating field. In a brain operation, and in correcting the trauma of a head wound, the surgeon must often operate in an extremely small field. When using conventional clamps the field becomes cluttered to the point that the operation is impeded. Moreover, available clamps often crush, cut or otherwise damage the blood vessels which they engage. Conventional designs of clamps are not amenable to reduction in size and level of clamping force; for example, conventional clamps, when reduced in size, become extremely difficult to manipulate.

It is, accordingly, an object of the present invention to provide a miniature surgical clip for clamping blood vessels in brain surgery and the like which may be made in extremely small sizes, down to a few millimeters in maximum dimension, but which is nonetheless, easy to manipulate, that is, apply and remove, either by a mechanical applicator or by the fingertips.

It is another object to provide a surgical clip for a small blood vessel which applies a clamping force which is proportioned to the size of the clip and which is sufficiently low as to prevent inadvertent crushing or other damage to the vessel. It is a related object to provide a surgical clip which may be made in extremely miniaturized form for use with the smallest of blood vessels but which may, nevertheless, be scaled up in size as may be desired for use with blood vessels of larger size and in other parts of the body.

It is an important object of the invention to provide a clip having opposed jaws and which is perfectly reliable in operation with means for maintaining the jaws in precisely opposed relation when the clip is both open and closed.

It is a more specific object to provide a surgical clip which is easily engageable by an applicator of the "tweezer" type, and which permits secure holding by the applicator to prevent inadvertent loss of the clip in the wound. It is, nevertheless, an object of the present invention to provide a clip which is intended to be used with a mechanical applicator but which may be conveniently applied by the fingertips of the surgeon. Regardless of whether the clip is applied by applicator or by fingertip, overstressing of the clip by excessively opening the jaws is avoided thereby protecting the integrity of the clip and preserving the calibration of the clamping force.

It is a general object of the invention to provide a miniature surgical clip made of a single continuous length of spring wire and which cannot, therefore, come apart in the wound as may happen with clips of multi-part construction.

A surgical clip generally providing the above objectives is disclosed in my earlier U.S. Pat. No. 4,444,187, which relates to a surgical clip having a pair of opposed arms adapted to releasably clamp a blood vessel. The arms are each made of a portion of spring wire which is doubled back on itself to provide a duck bill jaw element. In my prior patented clip, each of the opposed arms is captured in a guideway formed by two base legs of the clip extending substantially perpendicular to the direction of extension of the arms. In the improved clip described and claimed herein, one arm of the clip doubles back on itself and captures a single base leg of the clip, which single base leg acts as a guide for the movement of the doubled-backed arm element. Any tendency for the arms to slide past each other while in use is thereby eliminated. Therefore, an important object of the present invention is to provide a surgical clip having opposed movable jaws and guide means for one of the jaws which cooperate to prevent the possibility of one arm sliding or scissoring past the other during use, and thus inadvertently disconnecting the clip.

Finally, it is an object of the invention to provide a surgical clip which is of economical construction, which may be easily and quickly made by the bending of wire in a jig on a production line at extremely low cost, and which may therefore, be considered as a disposable item.

Other objects and advantages of the invention will become apparent upon reading the attached detailed description and upon reference to the drawings in which.

Figure 1:
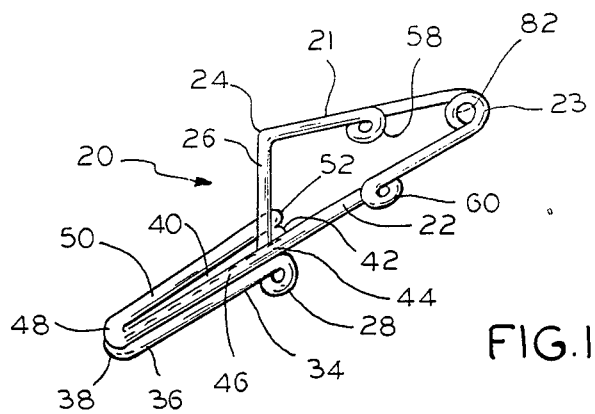
FIG. 1 is an enlarged perspective view of a clip constructed in accordance with the present invention.
Figure 3:
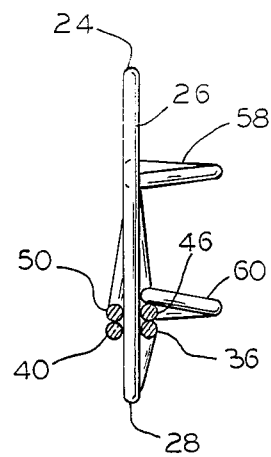
FIG. 3 is an end view looking along the line 3—3 in FIG. 2.
Figure 10:
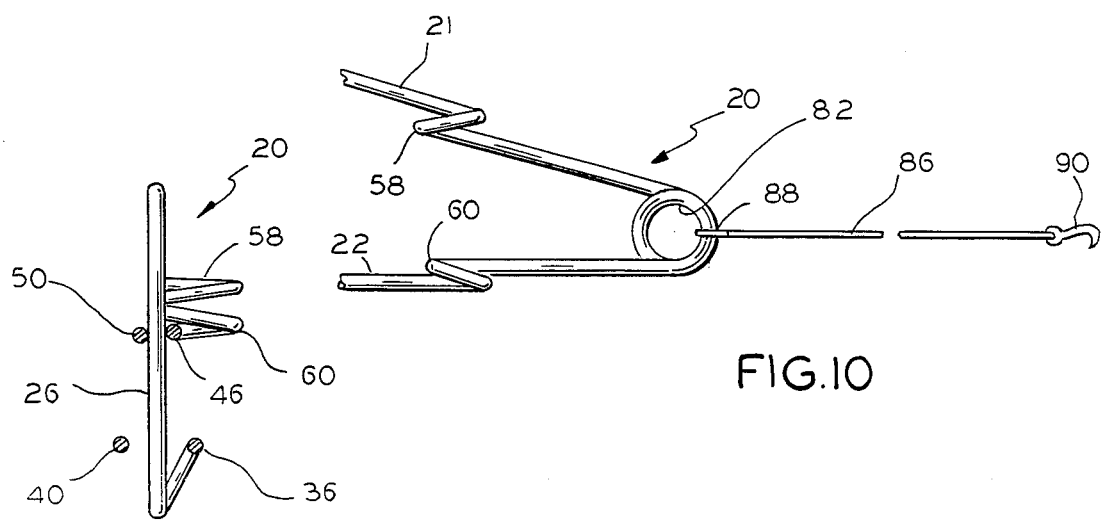
Figure 11:

FIG. 10 is a fragmentary view showing a hook and teather assembly attached to one end of the clip for the purpose of holding the clamped blood vessel back during a surgical procedure; and FIG. 11 is a view similar to FIG. 3, showing the arms of the clip in an open position, of another embodiment of the present invention which provides a nesting relationship between the two jaw elements of the clamp.

Referring now to the drawings and particularly to FIGS. 1-4, there is shown a miniature surgical clip 20 made of a single continuous length of spring material, such as wire or the like including a pair of operating members 21, 22 integrally connected at a common apex 23. The portions 21, 22 of the clip are referred to a "operating members" since it is pressure applied mutually inwardly on these members which results in the open and closing movements of the jaws to be described.

Figure 2:
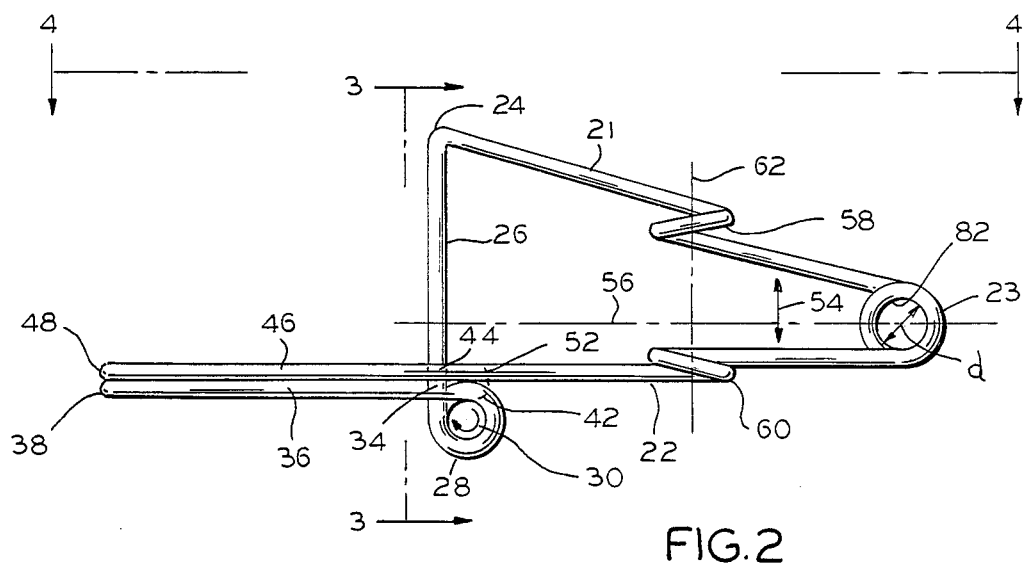
FIG. 2 is a plan view of the clip shown in FIG. 1.
Figure 4:
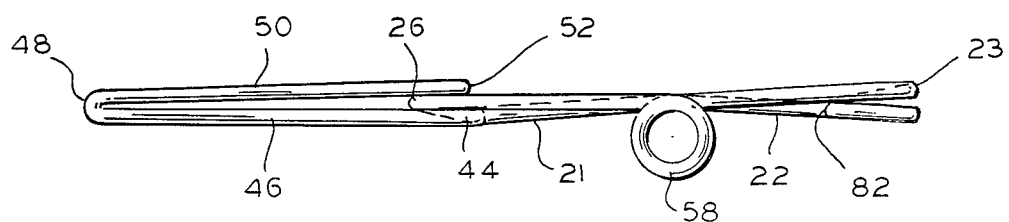
FIG. 4 is a top view looking along line 4—4 in FIG. 2.

Taking first the operating member 21, it is bent at 24 to form a base leg forming a guide element 26 which has an exit loop 28 which, as illustrated, is bent at an angle of 270°, as indicated at 30 (FIG. 2). Operating member 21 includes a straight exiting portion 34 terminating in a jaw 36 having a tip 38 which is sharply bent upon itself to provide a duck bill jaw element 40. The end 42 of jaw element 40 extends past guide element 26 and grips guide element 26 between end 42 and the portion of exiting portion 34 somewhat adjacent exit loop 28.

The operating element 22 on the other side of the clip has a jaw element 44 which extends beyond guide element 26 and terminates in a jaw 46 having a tip 48 which is sharply bent upon itself to provide a duck bill jaw element 50. The end 52 of jaw element 50 extends back beyond guide element 26 and slidingly grips guide element 26 between end 52 and the portion of jaw element 44 passing along the other side of guide element 26. As will be explained, jaw element 44 and jaw 46 are adapted to move up and down along guide element 26, which controls and constricts the lateral or sideways movement of jaw 46 to maintain jaws 36 and 46 in precise opposition to one another in both the open and closed position of the jaws.

In carrying out the present invention, the operating members 21, 22 are prestressed outwardly away from one another in the direction of the arrows 54 (FIG. 2) so that the exiting portions 34, 44 of the operating members, and the jaw elements 40, 50 are all bottomed mutually inwardly upon one another so that the clip 20 is biased into a normally closed position.

Each of the operating members 21, 22 has formed at its mid-portion an integral 360° applicator loop perpendicular to a plane 56, (FIG. 2), the loops being in axial alignment with one another for engagement by the tweezer type applicator shortly to be described or, alternatively, for engagement by the fingertips of the surgeon where a direct manual application is preferred. Thus, as particularly visible in FIG. 2, the applicator member 21 has a loop 58 formed therein, while the applicator member 22 has an applicator loop 60, the two loops being positioned opposite one another symmetrically with respect to a transverse axis 62.

For the purpose of applying the clip to a blood vessel, an applicator is provided in the form of a clamp having tips terminating in axially opposed sharpened points dimensioned to fit the respective applicator loops for application of a mutually inward force upon the operating members for temporarily spreading the jaws apart for engagement of a blood vessel between them, cooperating stops being provided on the tips of the applicator for limiting the approach of the points to one another, thereby to limit the degree of spread of the jaws to prevent overstressing the clip. Such a clamp, for convenience, is referred to herein as being of the "tweezer" type.

Figure 5:
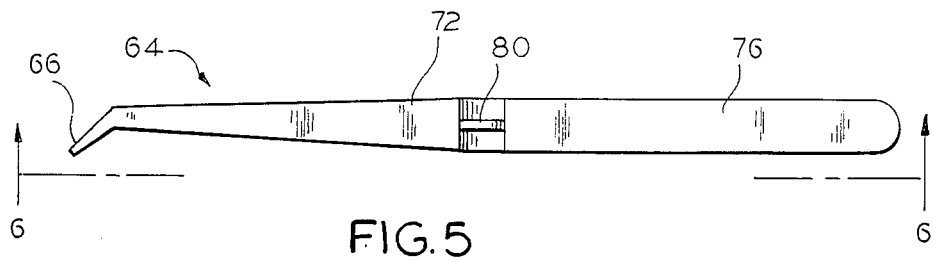
FIG. 5 shows an applicator of the tweezer type usable with the clip of the preceding figures and as viewed, in full size, from the flat side.
Figure 6:
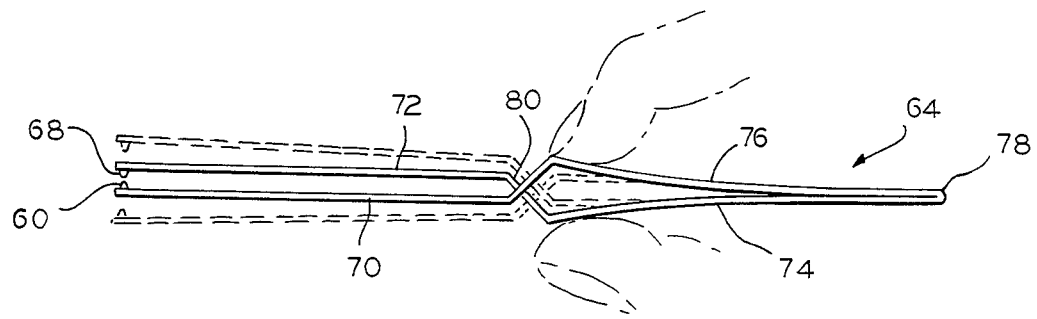
FIG. 6 shows the applicator as viewed edgewise along line 6—6 in FIG. 5.

Referring to FIGS. 5 and 6, the applicator, indicated at 64, has sharpened points 66, 68 which are in opposition to one another and which are respectively mounted upon blades 70, 72 of the tweezer, the blades being connected to pressure pads 74, 76 respectively, which are connected at their base ends to one another at 78, with respect to which they are outwardly sprung, with a "cross-over" at 80 to produce force reversal.

Figure 7:
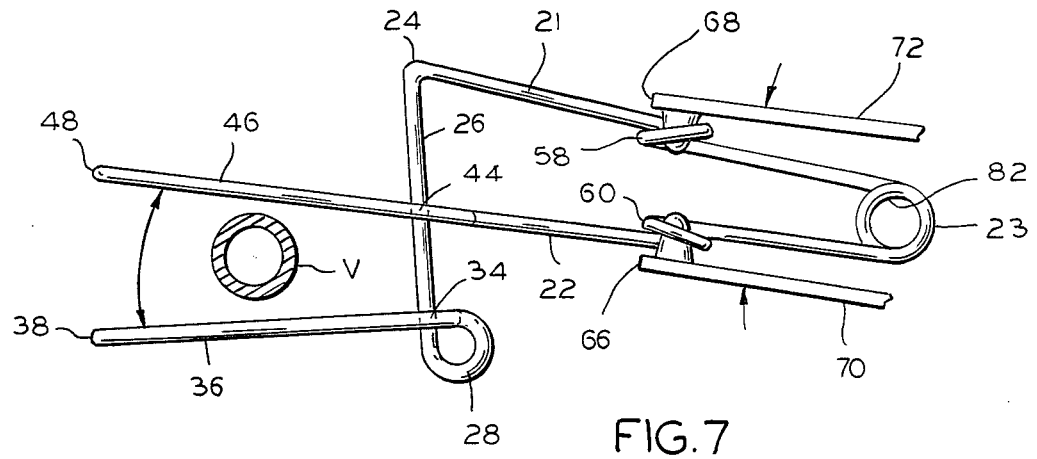
FIG. 7 is a view similar to FIG. 2 but showing the clip engaged by the applicator with the jaws spread apart for engagement of a blood vessel.
Figure 8:
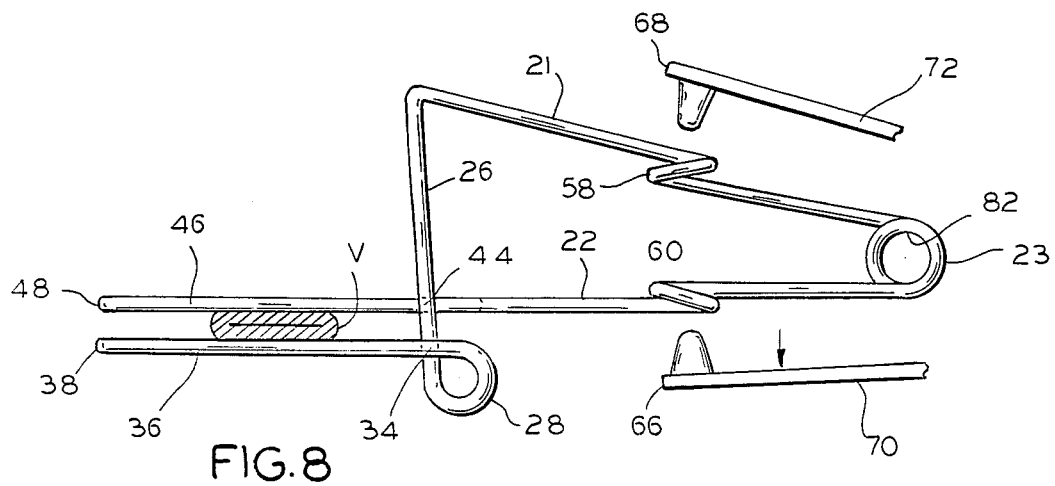
FIG. 8 is a view similar to FIG. 7 but showing the jaws in clamping engagement with the blood vessel.

In use, the tweezer applicator 64 is gripped at the pads 74, 76. Application of manual pressure, to press the pads together (as shown by dotted line in FIG. 6), spreads the points 66, 68 so that they may be engaged with the applicator loops 58, 60 on the clip. Since the pads 74, 76 are outwardly sprung at their point of connection 78, when the manual pressure on the tweezer is released, the points 66, 68 come together, overpowering the clip and spreading the jaws 36, 46 of the clip 20 apart so that the jaws may be placed in straddling relation to a blood vessel V (see FIG. 7). Release of the pressure applied to the pads 74, 76 on the tweezer permits the points 66, 68 to come together, engaging the applicator loops and spreading the jaws of the clip. When manual force is reapplied to the pads 74, 76 to spread the points 66, 68 to release the clip, the jaws of the clip will re-close upon the blood vessel with a predetermined force (FIG. 8), thereby avoiding any possibility of crushing or cutting the tender vessel.

One of the features of the present invention is to constrain lateral movement of jaw 46 as jaw 46 slides along guide element 26, and to maintain the jaw elements 36, 46 precisely opposed to one another whereby jaw 46 cannot slip past jaw 36, scissor fashion, which might cause the blood vessel which is intended to be clamped to be severed. It is a further feature of the present invention that while clamps of conventional design do no lend themselves well to scaling downwardly in size, the present design of small clips can be scaled upwardly in size for use on larger blood vessels both in the brain and in other parts of the body.

Figure 9:
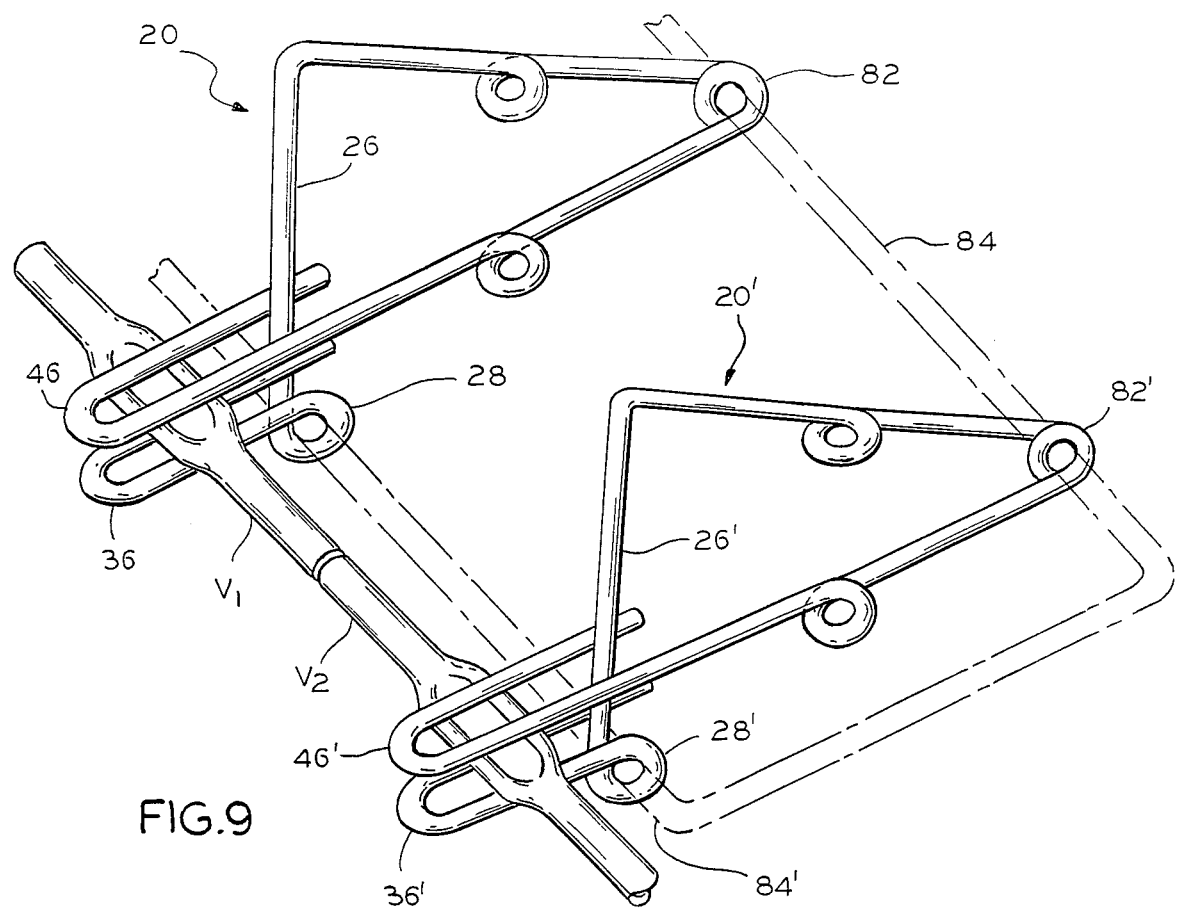
FIG. 9 shows, in side view, two of the clips fitted side by side on a rod to form an "approximator" holding the severed holding ends of a blood vessel adjacent one another for suturing together.

In accordance with one of the features of the present invention, an apex loop in excess of 360° may be formed at the apex 23, permitting at least two of the clips to be strung on a rod which is snuggly fitted in the respective apex loops, the clips being spaced in parallel side-by-side relation for engagement, by their respective jaws, of the opposed ends of a severed blood vessel for holding the ends of the blood vessel in axial alignment as the ends are sutured together. Thus as disclosed in FIGS. 1-4 there is provided, at the apex 23, an apex loop 82 having an inner diameter d. This permits two of the clips to be mounted side-by-side on a rod 84 as shown in FIG. 9, the clips 20 and 20' being rather snugly fitted on the rod so as to hold, conveniently adjacent one another, the severed ends V1, V2 of a blood vessel while the surgeon stitches the ends of the vessel together. If desired the rod may be of "U" shape having a reversely bent portion 74' which is entered in the loops 28, 28' to keep the clips aligned, with their jaws in a common plane.

FIG. 10 illustrates an additional advantageous feature of the structure of the present invention. A teather 86 may be attached or releasably hooked as at 88 to apex loop 82. A small hook 90 is attached to the other end of teather 86. If desired, after a blood vessel is clamped with clip 20, pressure is applied to teather 86 to pull the clip 20 and the attached blood vessel back out of the way to enable a surgical procedure to be performed in the area previously occupied by the vessel. To maintain the vessel out of the way, hook 90 is embedded in some other part of the anatomy which is anesthetized and unaffected by the minute penetration of hook 90.

FIG. 11 schematically illustrates an embodiment of the invention providing a nesting relationship between jaw 36 and jaw 46. In this embodiment, the jaw 36 and its associated double-backed duck bill jaw element 40 are separated a distance away from guide element 26 a distance equal to slightly more than the diameter of the spring wire forming clip 20. Thus, when movable jaw 46 (shown in its open or raised position in FIG. 11) is moved to its closed position, jaw 46 and its associated doubled-backed duck bill jaw element 50 will nest in the space between jaw elements 36 and 40. This tends to provide a firmer clamping force for the blood vessel.

The present design provides high degree of flexibility in the specific design of clips for blood vessels of different size. The size, which may be as small as three to five millimeters in major dimension, provides optimum clamping force on the order of 5 grams for blood vessels of smallest size, with the dimensions being scaled upwardly for vessels of greater size. For each size the amount of clamping force may be preselected based upon the stiffness (spring rate) of the spring wire and the amount of outward pre-stress indicated by the arrows 54 in FIG. 2. If desired the clips may be calibrated in accordance with the degree of clamping force which they exert and segregated accordingly for later use. A calibrating device may be used as disclosed in my U.S. Pat. No. 4,353,250.

The construction amply meets the objects set forth above: The clip exerts a predetermined safe level of clamping force, may be calibrated in accordance with the clamping force, and retains such calibration, and full structural integrity in spite of repeated usage. The opposed jaws are maintained in direct opposition when the clip is both open and closed, and scissoring is prevented. The clip is easily applied by an applicator which is so constructed as to prevent inadvertent loss of the clip in the wound, although the clip may be applied, if desired, by fingertip pressure without affecting its clamping force and with no risk of overstress. The clip is of economical construction, easily and economically formed on a production line basis, and made of a single piece of wire for maximum safety in the wound.

The jaws 36, 46, as illustrated, are both formed of wire reversely bent (at the tips 38, 48) to provide a "full" duckbill to distribute the clamping force. However, if desired, and as apparent to one skilled in the art, only one of the jaws need have the reverse bend; the other may be straight and centered with respect thereto resulting in a "semi"duckbill.

Also while it is preferred to have the jaws lie in the plane of the clip, the jaw 36 may, if desired, be bent so as to extend upwardly through the reverse bent jaw 46, or to extend off to one side, or the jaws may occupy any angular position. Clips constructed with the upward bend would be of particular use in clasping directly onto the skin of the surgical patient. The term "straight" is intended to include jaws which are substantially straight, i.e., having slight curvature.

I claim:

1. A miniature surgical clip made of a single continuous length of spring material comprising, in combination, first and second operating members arranged at an acute angle with respect to one another connected together at a common apex, said first operating member having an inwardly bent base leg which defines a guide element and a first jaw member which extends from said base leg in a direction away from said common apex, said second operating member having a portion defining a second jaw member which extends adjacent to and beyond said guide element in a direction away from said common apex and substantially parallel to said first jaw member to form cooperating jaws which are straight and parallel, said second jaw member including an additional portion thereof which is sharply bent back along said second jaw member and slidingly grasps said guide element between said second jaw member and said additional portion, said operating members being outwardly sprung with respect to one another for biasing said first and second jaw members resiliently into clamping engagement whereby when a mutually inward force is applied to the operating members, said first and second jaw members are spread apart for engagement of a blood vessel between them, and whereby, when said mutually inward force is released, said second jaw member is guided by said guide element towards said first jaw member and into directly opposed clamping engagement with said blood vessel said first jaw member including an additional portion thereof which is sharply bent back along said first jaw member whereby said guide element is disposed between said first jaw member and said additional portion of said first jaw member.

2. The miniature surgical clip of claim 1 wherein said inwardly bent base leg terminates in a 270° exit loop having a straight exit portion which forms said first jaw member.

3. The miniature surgical clamp of claim 1 wherein said gude element is firmly gripped between said first jaw member and said additional portion of said first jaw member.

4. The miniature surgical clamp of claim 1 wherein said first jaw member and said additional portion of said first jaw member are each laterally separated from said guide element by a distance at least equal to the diameter of said spring wire.

5. The miniature surgical clip of claim 1 wherein each of said operating members include an integral 360° applicator loop formed in axial alignment at the midportion of each said operating member and perpendicular to the direction of extent of said guide element.

* * * * *